United States Patent [19]

Ayres et al.

[11] 4,315,005

[45] Feb. 9, 1982

[54] CEPHALOSPORIN ANTIBIOTICS

[75] Inventors: Barry E. Ayres, Ickenham; Niall G. Weir, Wembley, both of England

[73] Assignee: Glaxo Group Limited, London, England

[21] Appl. No.: 132,644

[22] Filed: Mar. 21, 1980

[30] Foreign Application Priority Data

Mar. 22, 1979 [GB] United Kingdom ............... 10088/79
Sep. 24, 1979 [GB] United Kingdom ............... 32982/79

[51] Int. Cl.³ .................. A61K 31/545; C07D 501/56
[52] U.S. Cl. ........................................ 424/246; 544/25
[58] Field of Search ........................... 544/25; 424/246

[56] References Cited

U.S. PATENT DOCUMENTS

| | | | |
|---|---|---|---|
| 4,033,950 | 7/1977 | Cook et al. | 424/246 |
| 4,098,888 | 7/1978 | Ochiai et al. | 544/25 |
| 4,103,084 | 7/1978 | Bradshaw et al. | 544/22 |
| 4,144,392 | 3/1979 | Bradshaw et al. | 544/27 |
| 4,152,432 | 5/1979 | Heymes et al. | 424/246 |
| 4,166,115 | 8/1979 | Takaya et al. | 544/27 |
| 4,278,793 | 7/1981 | Durckheimer et al. | 544/27 |

FOREIGN PATENT DOCUMENTS

| | | |
|---|---|---|
| 866422 | 10/1978 | Belgium . |
| 1664 | 3/1977 | South Africa . |
| 2030 | 3/1977 | South Africa . |
| 847 | 2/1978 | South Africa . |
| 1502 | 3/1978 | South Africa . |
| 1630 | 3/1978 | South Africa . |

OTHER PUBLICATIONS

Tsuchiya et al., Antimicrobial Agents and Chemotherapy 14(4), 557–568 (1978).
Numata et al., J. Antibiotics XXXI (12), 1262–1271 (1978).
Heymes et al., C. R. Acad. Sc., 248, 1847 (1977).
Ochiai et al., Chem. Pharm. Bull. 25(11), 3115–3119 (1977).
Heymes et al., Tetrahedron 34, 2233–2243 (1978).
Hamilton-Miller et al., J. Antimicrobial Chemistry 4, 437–444 (1978).

Primary Examiner—Paul M. Coughlan, Jr.
Attorney, Agent, or Firm—Bacon & Thomas

[57] ABSTRACT

Cephalosporin antibiotics of general formula

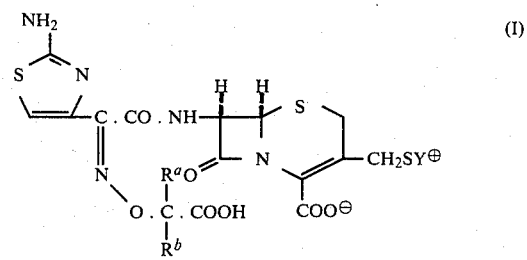

(wherein $R^1$ and $R^b$, which may be the same or different, each represent a $C_{1-2}$ alkyl group, or together with the carbon atom to which they are attached form a $C_{3-6}$ cycloalkylidene group and $Y^\oplus$ represents a 1-carbamoylmethylpyridinium group) exhibit broad spectrum antibiotic activity, the activity being unusually high against gram-negative organisms such as strains of Pseudomonas organisms.

Particularly effective compounds of formula (I) are (6R,7R)-7-[(Z)-2-(2-aminothiazol-4-yl)-2-(2-carboxyprop-2-oxyimino)acetamido]-3-[(1-carbamoylmethylpyridinium-4-yl)thiomethyl]ceph-3-em-4-carboxylate and (6R,7R)-[(Z)-2-(2-aminothiazol-4-yl)-2-[(1-carboxycyclobut-1-oxyimino)acetamido]-3-[(1-carbamoylmethylpyridinium-4-yl)thiomethyl]-ceph-3-em-4-carboxylate. The invention also includes the non-toxic salts and non-toxic metabolically labile esters of compounds of formula (I), compositions containing the antibiotic compounds of the invention and processes for the preparation of the antibiotics.

9 Claims, No Drawings

CEPHALOSPORIN ANTIBIOTICS

This invention is concerned with cephalosporin compounds possessing valuable antibiotic properties.

The cephalosporin compounds in this specification are named with reference to "cepham" after *J. Amer. Chem. Soc.*, 1962, 84, 3400, the term "cephem" referring to the basic cepham structure with one double bond.

Cephalosporin antibiotics are widely used in the treatment of disease caused by pathogen bacteria in human beings and animals, and are especially useful in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram-positive and gram-negative microorganisms, and a significant amount of research has been directed to the development of various types of broad spectrum cephalosporin antibiotics.

We have now discovered that by an appropriate selection of a small number of particular groups at the 7β-position in combination with an N-carbamoylmethylpyridiniumthiomethyl group at the 3-position, compounds having particularly good activity (described in more detail below) against a wide range of commonly encountered pathogenic organisms may be obtained.

The present invention provides cephalosporin antibiotics of the general formula:

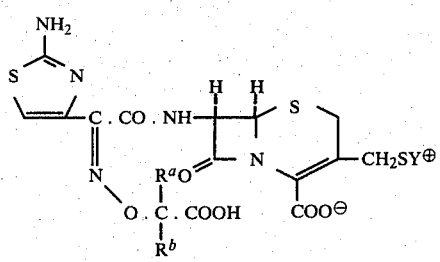

(I)

(wherein $R^a$ and $R^b$, which may be the same or different, each represents a $C_{1-2}$ alkyl group or together with the carbon atom to which they are attached, form a $C_{3-6}$ cycloalkylidene group and $Y^{\oplus}$ represents an N-carbamoylmethylpyridinium group) and non-toxic salts and non-toxic metabolically labile esters thereof.

The compounds according to the invention are syn isomers. The syn isomeric form is defined by the configuration of the group

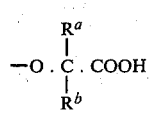

with respect to the carboxamido group. In this specification the syn configuration is denoted structurally as

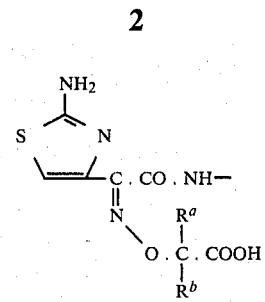

It will be understood that the compounds according to the invention are geometric isomers and some admixture with the corresponding anti isomer may occur.

The invention also includes within its scope the solvates (especially the hydrates) of the compounds according to the invention. It also includes within its scope salts of esters of compounds of formula (I).

It will be appreciated that the N-carbamoylmethylpyridinium group may be attached to the sulphur atom via the 2-, 3- or 4-carbon atom of the pyridine ring.

The compounds according to the present invention may exist in tautomeric forms (for example in respect of the 2-aminothiazolyl group) and it will be understood that such tautomeric forms, e.g. the 2-iminothiazolinyl form, are included within the scope of the invention. Moreover, the compounds of formula (I) depicted above may also exist in alternative zwitterionic forms, for example wherein the 4-carboxyl group is protonated and the terminal carboxyl group in the 7-side chain is deprotonated. Such zwitterionic forms and mixtures thereof are included within the scope of the present invention.

It will also be appreciated that when one of $R^a$ and $R^b$ in formula (I) represents a methyl group and the other represents an ethyl group, the carbon atom to which they are attached will comprise a centre of asymmetry. Such compounds are diastereoisomeric and the present invention embraces individual diasteroisomers of these compounds as well as mixtures thereof.

The compounds according to the invention exhibit broad spectrum antibiotic activity. Against gram-negative organisms the activity is unusually high. This high activity extends to many β-lactamase-producing gram-negative strains. The compounds also possess high stability to β-lactamases produced by a range of gram-positive and gram-negative organisms.

Compounds according to the invention have been found to exhibit unusually high activity against strains of *Pseudomonas* organisms, e.g. strains of *Pseudomonas aeruginosa* as well as high activity against various members of the Enterobacteriaceae (e.g. strains of *Escherichia coli, Klebsiella pneumoniae, Salmonella typhimurium, Shigella sonnei, Enterobacter cloacae, Serratia marcescens, Providence species, Proteus mirabilis* and especially indole-positive Proteus organisms such as *Proteus vulgaris* and *Proteus morganii*), and strains of *Haemophilus influenzae*.

The antibiotic properties of the compounds according to the invention compare very favourably with those of the aminoglycosides such as amikacin or gentamicin. In particular, this applies to their activity against strains of various *Pseudomonas* organisms which are not susceptible to many existing commercially available antibiotic compounds. Unlike the aminoglycosides, cephalosporin antibiotics normally exhibit low toxicity in man. The use of aminoglycosides in human therapy tends to be limited or complicated by the relatively high toxicity of these antibiotics. The cephalosporin antibiotics of the present invention thus possess potentially great advantages over the aminoglycosides.

Non-toxic salt derivatives which may be formed from the compounds of general formula (I) include inorganic base salts such as alkali metal salts (e.g. sodium and potassium salts) and alkaline earth metal salts (e.g. calcium salts); amino acid salts (e.g. lysine and arginine salts); organic base salts (e.g. procaine, phenethylbenzylamine, dibenzylethylenediamine, ethanolamine, diethanolamine and N-methyl-glucosamine salts). Other non-toxic salt derivatives include acid addition salts, e.g. formed with hydrochloric, hydrobromic, sulphuric, nitric, phosphoric, formic and trifluoroacetic acids. The salts may also be in the form of resinates formed with, for example, a polystyrene resin or crosslinked polystyrene divinylbenzene copolymer resin containing amino or quaternary amino groups or sulphonic acid groups, or with a resin containing carboxyl groups, e.g. a polyacrylic acid resin. Soluble base salts (e.g. alkali metal salts such as the sodium salt) of compounds of formula (I) may be used in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

These and other salt derivatives such as the salts with toluene-p-sulphonic and methanesulphonic acids may be employed as intermediates in the preparation and/or purification of the present compounds of formula (I), for example in the processes described below.

Non-toxic metabolically labile ester derivatives which may be formed from the parent compound of formula (I) include acyloxyalkyl esters, e.g. lower alkanoyloxymethyl or -ethyl esters such as acetoxymethyl or -ethyl or pivaloyloxymethyl esters. In addition to the above ester derivatives, the present invention includes within its scope compounds of formula (I) in the form of other physiologically acceptable equivalents, i.e. physiologically acceptable compounds which, like the metabolically labile esters, are converted in vivo into the parent antibiotic compound of formula (I).

Preferred compounds according to the invention include those compounds of formula (I) wherein $Y^\oplus$ represents a 1-carbamoylmethylpyridinium-4-yl group. Preference is also expressed for those compounds wherein $R^a$ and $R^b$ both represent methyl groups or together with the carbon atom to which they are attached form a cyclobutylidene group.

Particularly preferred compounds according to the invention are (6R, 7R)-7-[(Z)-2-(2-aminothiazol-4-yl)-2-(2-carboxyprop-2-oxyimino)acetamido]-3-[(1-carbamoylmethylpyridinium-4-yl)thiomethyl]ceph-3-em-4-carboxylate and (6R, 7R)-7-[(Z)-2-(2-aminothiazol-4-yl)-2-(1-carboxycyclobut-1-oxyimino)acetamido]-3-[(1-carbamoylmethylpyridinium-4-yl)thiomethyl]ceph-3-em-4-carboxylate, and their non-toxic salts and non-toxic metabolically labile esters. These particularly preferred compounds possess to an outstanding extent the general antibiotic properties set out above for the compounds of formula (I). However one may emphasise their excellent activity against strains of Pseudomonas. The compounds also possess useful activity against strains of Staphylococcus aureus. The compounds have excellent antibacterial properties which generally are not impaired by human serum and, moreover, the effect of increased inocula against the compounds is low. The serum half-life in primates points to the probability of a comparatively long half-life in man, with the possibility of less frequent dosages being required for less serious infections. They are well distributed in the bodies of small rodents giving useful therapeutic levels after subcutaneous injection. Experimental infections in mice with gram-negative bacteria were successfully treated using the compounds and, in particular, good protection was obtained against strains of Pseudomonas aeruginosa, an organism normally not susceptible to treatment with cephalosporin antibiotics. The protection was comparable with the treatment with an aminoglycoside such as amikacin. Administration of 500 mg/kg of either compound to mice did not cause any deaths, indicating an $LD_{50}$ in excess of this figure.

The above described compounds according to the invention may be used for treating a variety of diseases caused by pathogenic bacteria in human beings and animals, such as respiratory tract infections and urinary tract infections.

According to a further embodiment of the present invention we provide a process for the preparation of compounds of formula (I) as hereinbefore defined or non-toxic salts or non-toxic metabolically labile esters thereof which comprises (A) reacting a compound of the formula

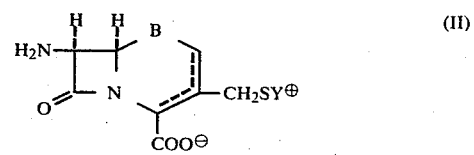

[wherein $Y^\oplus$ is as hereinbefore defined, B is $>S$ or $>S \rightarrow O$ ($\alpha$- or $\beta$-) and the dotted line bridging the 2-, 3- and 4-positions indicates that the compound is a ceph-2-em or ceph-3-em compound], or an acid addition salt (formed with, for example, a mineral acid such as hydrochloric, hydrobromic, sulphuric, nitric or phosphoric acid or an organic acid such as methanesulphonic or toluene-p-sulphonic acid) or an N-silyl derivative thereof, or a corresponding compound possessing a group of the formula —COOR$^1$ at the 4-position where R$^1$ is a hydrogen atom or a carboxyl blocking group e.g. the residue of an ester-forming aliphatic or araliphatic alcohol or an ester-forming phenol, silanol or stannanol (the said alcohol, phenol, silanol or stannanol preferably containing 1 to 20 carbon atoms) and having an associated anion $A^\ominus$ such as a halide, e.g. chloride, bromide or iodide, or trifluoroacetate ion, with an acid of formula

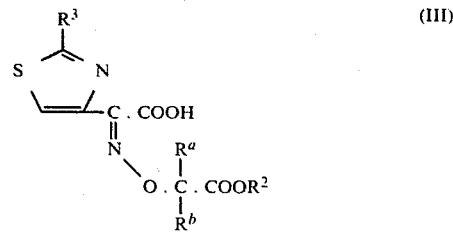

wherein R$^a$ and R$^b$ are as hereinbefore defined; R$^2$ represents a carboxyl blocking group (e.g. as described for $R^1$) and $R^3$ is an amino or protected amino group or with an acylating agent corresponding thereto, or (B) reacting a compound of formula

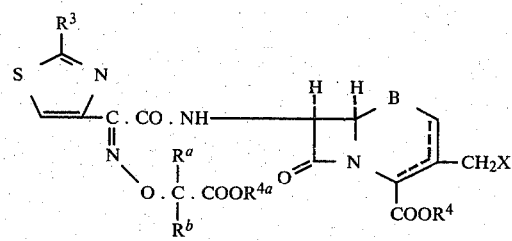
(IV)

(wherein $R^a$, $R^b$, $R^3$, B and the dotted line are as hereinbefore defined; $R^4$ and $R^{4a}$ may independently represent hydrogen or a carboxyl blocking group; and X is a replaceable residue of a nucleophile, e.g. an acetoxy or dichloroacetoxy group or a halogen atom such as chlorine, bromine or iodine) or a salt thereof, with a sulphur nucleophile serving to form the group $-CH_2SY^\oplus$ (wherein $Y^\oplus$ is as hereinbefore defined) at the 3-position; or (C) reacting a compound of the formula

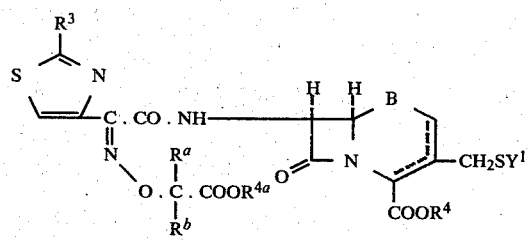
(V)

(wherein $R^a$, $R^b$, $R^3$, B and the dotted lines are as herebefore defined; $R^4$ and $R^{4a}$ in this instance are both carboxyl blocking groups and $Y^1$ represents a pyridyl group) with a carbamoylmethylating agent serving to introduce a carbamoylmethyl group as a substituent on the nitrogen atom of the pyridyl ring; whereafter, if necessary and/or desired in each instance, any of the following reactions, in any appropriate sequence, are carried out:

(i) conversion of a $\Delta^2$-isomer into the desired $\Delta^3$-isomer,
(ii) reduction of a compound wherein B is $>S\rightarrow 0$ to form a compound wherein B is $>S$,
(iii) conversion of a carboxyl group into a non-toxic salt or non-toxic metabolically labile ester function, and
(iv) removal of any carboxyl blocking and/or N-protecting groups.

Acylating agents which may be employed in the preparation of compounds of formula (I) include acid halides, particularly acid chlorides or bromides. Such acylating agents may be prepared by reacting an acid (III) or a salt thereof with a halogenating agent e.g. phosphorus pentachloride, thionyl chloride or oxalyl chloride.

Where an acid addition salt of the compound of formula (II) is used, this is generally treated with a base prior to reaction with the compound of formula (III) or an acylating agent corresponding thereto.

Acylations employing acid halides may be effected in aqueous and non-aqueous reaction media conveniently at temperatures of from $-50°$ to $+50°$ C. preferably $-20°$ to $+30°$ C., if desired in the presence of an acid binding agent. Suitable reaction media include aqueous ketones such as aqueous acetone, esters such as ethyl acetate, halogenated hydrocarbons such as dichloromethane, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula (III) may themselves be used as acylating agents in the preparation of compounds of formula (I). Acylations employing acids (III) are desirably conducted in the presence of a condensing agent, for example a carbodiimide such as N,N'-dicyclohexylcarbodiimide or N-ethyl-N'-$\gamma$-dimethylaminopropylcarbodiimide; a carbonyl compound such as carbonyldiimidazole; or an isoxazolium salt such as N-ethyl-5-phenylisoxazolium perchlorate.

Acylation may be effected with other amide-forming derivatives of acids of formula (III) such as, for example, an activated ester, a symmetrical anhydride or a mixed anhydride (e.g. formed with pivalic acid or with a haloformate such as a lower alkylhaloformate).

Mixed anhydrides may also be formed with phosphorus acids (for example, phosphoric or phosphorous acids), sulphuric acid or aliphatic or aromatic sulphonic acids (for example toluene-p-sulphonic acid).

An activated ester may conveniently be formed in situ using, for example, 1-hydroxybenzotriazole in the presence of a condensing agent as set out above. Alternatively, the activated ester may be preformed.

Acylation reactions involving the free acids or their above mentioned amide-forming derivatives are desirably effected in an anhydrous reaction medium e.g. dichloromethane, tetrahydrofuran, dimethylformamide or acetonitrile.

If desired, the above acylation reactions may be performed in the presence of a catalyst, e.g. 4-dimethylaminopyridine.

The amino acids of formula (III) and acylating agents corresponding thereto may, if desired, be prepared and employed in the form of their acid addition salts. Thus, for example, acid chlorides may conveniently be employed as their hydrochloride salts and acid bromides as their hydrobromide salts.

In process (B) above, the sulphur nucleophile may be used to displace a wide variety of substituents X from the cephalosporin of formula (IV). To some extent the facility of the displacement is related to the pKa of the acid HX from which the substituent is derived. Thus, atoms or groups X derived from strong acids tend, in general, to be more easily displaced than atoms or groups derived from weaker acids. The facility of the displacement is also related, to some extent, to the precise character of the sulphur nucleophile. The nucleophile may be employed, for example, in the form of a thiol or thione, and may be, for example an N-carbamoylmethylpyridthione.

The displacement of X by the sulphur nucleophile may conveniently be effected by maintaining the reactants in solution or suspension. The reaction is advantageously effected using from 1 to 10 moles e.g. 1 to 2 moles of the nucleophile.

Nucleophilic displacement reactions may conveniently be carried out on those compounds of formula (IV) wherein the substituent X is a halogen atom or an acyloxy group, for example as discussed below.

Acyloxy groups

Compounds of formula (IV) wherein X is an acetoxy group are convenient starting materials for use in the nucleophilic displacement reaction with the sulphur nucleophile. Alternative starting materials in this class include compounds of formula (IV) in which X is the residue of a substituted acetic acid e.g. chloroacetic acid, dichloroacetic acid and trifluoroacetic acid.

Displacement reactions on compounds of formula (IV) possessing X substituents of this class, particularly in the case where X is an acetoxy group, may be facilitated by the presence in the reaction medium of iodide or thiocyanate ions.

The substituent X may also be derived from formic acid, a haloformic acid such as chloroformic acid, or a carbamic acid.

When using a compound of formula (IV) in which X represents an acetoxy or substituted acetoxy group, it is generally desirable that the group $R^4$ in formula (IV) should be a hydrogen atom and that B should represent $>S$. In this case, the reaction is advantageously effected in an aqueous medium.

Under aqueous conditions, the pH value of the reaction solution is advantageously maintained in the range 6–8, if necessary by the addition of a base. The base is conveniently an alkali metal or alkaline earth metal hydroxide or bicarbonate such as sodium hydroxide or sodium bicarbonate.

When using compounds of formula (IV) in which X is an acetoxy group, the reaction is conveniently effected at a temperature of 30° C. to 110° C., preferably 50° C. to 80° C.

Halogens

Compounds of formula (IV) in which X is a chlorine, bromine or iodine atom can also be conveniently used as starting materials in the nucleophilic displacement reaction with the sulphur nucleophile. When using compounds of formula (IV) in this class, B may represent $>S\rightarrow0$ and $R^4$ may represent a carboxyl blocking group. The reaction is conveniently effected in a non-aqueous medium which preferably comprises one or more organic solvents, advantageously of a polar nature such as ethers, e.g. dioxan or tetrahydrofuran, esters, e.g. ethyl acetate, amides, e.g. formamide or N,N-dimethylformamide or ketones e.g. acetone. Other suitable organic solvents are described in more detail in British patent specification No. 1,326,531. The reaction medium should be neither extremely acidic nor extremely basic.

In the case of reactions carried out on compounds of formula (IV) in which $R^4$ and $R^{4a}$ are carboxyl blocking groups the products will be formed as the corresponding halide salts which may, if desired, be subjected to one or more ion exchange reactions to obtain salts having the desired anion.

When using compounds of formula (IV) in which X is a halogen atom as described above, the reaction is conveniently effected at a temperature of $-20°$ to $+60°$, preferably 0° to $+30°$ C.

In process (C) above, the 3-pyridylthiomethyl compound of formula (V) is advantageously reacted with a carbamoylmethylating agent of the formula $H_2NCOCH_2Z$ where Z is a leaving group such as a halogen atom (e.g. iodine, chlorine or bromine) or a hydrocarbyl sulphonate (e.g. mesylate or tosylate) group. Iodoacetamide is preferred as the carbamoylmethylating agent. The reaction is preferably carried out at a temperature in the range of 0° to 60° C., advantageously 20° to 30° C. The reaction may be conveniently effected in an inert solvent such as an ether e.g. tetrahydrofuran, an amide, e.g. dimethylformamide, a lower alkanol e.g. ethanol, a lower dialkylketone, e.g. acetone, a halogenated hydrocarbon e.g. dichloromethane or chloroform, or an ester, e.g. ethyl acetate.

The 3-pyridylthiomethyl compound of formula (V) used as starting material in process (C) may be prepared for example by reaction of a compound of formula (IV) (as defined above) with an appropriate sulphur nucleophile (e.g. pyrid-4-thione) in an analogous manner to the nucleophilic displacement reaction described with respect to process (B). When X in formula (IV) is halogen, the reaction is preferably effected in the presence of an acid scavenging agent, for example a base such as triethylamine or calcium carbonate. If desired the above nucleophile may be used in the form of a metal thiolate salt.

The reaction product may be separated from the reaction mixture, which may contain, for example, unreacted nucleophile and other substances, by a variety of processes including recrystallisation, ionophoresis, column chromatography and use of ion-exchangers (for example by chromatography on ion-exchange resins) or macroreticular resins.

A $\Delta^2$-cephalosporin ester derivative obtained in accordance with the process of the invention may be converted into the corresponding $\Delta^3$-derivative by, for example, treatment of the $\Delta^2$-ester with a base such as pyridine or triethylamine.

A ceph-2-em reaction product may also be oxidised to yield the corresponding ceph-3-em 1-oxide, for example by reaction with a peracid e.g. peracetic or m-chloro-perbenzoic acid; the resulting sulphoxide may, if desired, subsequently be reduced as described hereinafter to yield the corresponding ceph-3-em sulphide.

Where a compound is obtained in which B is $>S\rightarrow0$ this may be converted into the corresponding sulphide by, for example, reduction of the corresponding acyloxy-sulphonium salt prepared in situ by reaction with e.g. acetyl chloride in the case of an acetoxy-sulphonium salt, reduction being effected by, for example, sodium dithionite or by iodide ions as in a solution of potassium iodide in a water miscible solvent e.g. acetic acid, acetone, tetrahydrofuran, dioxan, dimethylformamide or dimethylacetamide. The reaction may be effected at a temperature between $-20°$ to $+50°$ C.

Metabolically labile ester derivatives of the compounds of formula (I) may be prepared by reacting a compound of formula (I) or a salt or protected derivative thereof with the appropriate esterifying agent such as an acyloxymethyl halide (e.g. iodide), conveniently in an inert organic solvent such as dimethylformamide or acetone, followed, where necessary, by removal of any protecting groups.

Base salts of the compounds of formula (I) may be formed by reacting an acid of formula (I) with an appropriate base. Thus, for example, sodium or potassium salts may be prepared using the respective 2-ethylhexanoate or hydrogen carbonate salts. Acid addition salts may be prepared by reacting a compound of formula (I) or a metabolically labile ester derivative thereof with the appropriate acid.

Where a compound of formula (I) is obtained as a mixture of isomers, the syn isomer may be obtained by, for example, conventional methods such as crystallisation of chromatography. Syn and anti isomers may be distinguished by appropriate techniques, e.g. by thin layer, paper or high pressure liquid chromatography or by their proton magnetic resonance spectra.

For use as starting materials for the preparation of the compounds of formula (I) according to the invention, compounds of general formula (III) and acid halides and anhydrides corresponding thereto in their syn isomeric form, or in the form of mixtures of the syn isomers and the corresponding anti isomers containing at least 90% of the syn isomer, are preferably used.

Acids of formula (III) (provided that $R^a$ and $R^b$ together with the carbon atom to which they are attached do not form a cyclopropylidene group) may be prepared by etherification of a compound of formula

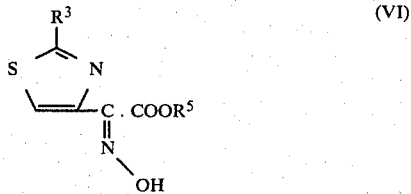

(VI)

(wherein $R^3$ is as hereinbefore defined and $R^5$ represents a carboxyl blocking group) by reaction with a compound of general formula

(VII)

(wherein $R^a$, $R^b$, and $R^2$ are as hereinbefore defined and T is halogen such as chloro, bromo, or iodo; sulphate; or sulphonate such as tosylate) followed by removal of the carboxyl blocking group $R^5$.

Acids of general formula (III) may also be prepared by reaction of a compound of formula

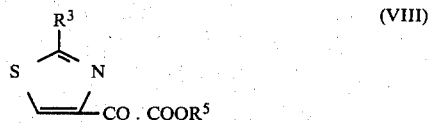

(VIII)

(wherein $R^3$ and $R^5$ are as hereinbefore defined) with a compound of formula

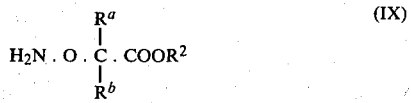

(IX)

(wherein $R^a$, $R^b$ and $R^2$ are as defined above), followed by removal of the carboxyl blocking group $R^5$.

The last mentioned reaction is particularly applicable to the preparation of acids of formula (III) wherein $R^a$ and $R^b$ together with the carbon atom to which they are attached form a cyclopropylidene group.

These methods of preparing the acids are described in more detail in Belgian Pat. No. 876,538.

The acids of formula (III) may be converted into the corresponding acid halides and anhydrides and acid addition salts by conventional methods.

Where X is a halogen (i.e. chlorine, bromine or iodine) atom in formula (IV), ceph-3-em starting compounds may be prepared in conventional manner, e.g. by halogenation of a 7β-protected amino-3-methylceph-3-em-4-carboxylic acid ester 1β-oxide, removal of the 7β-protecting group, acylation of the resulting 7β-amino compound to form the desired 7β-acylamido group, e.g. in an analogous manner to process (A) above, followed by reduction of the 1β-oxide group later in the sequence. This is described in British Pat. No. 1,326,531. The corresponding ceph-2-em compounds may be prepared by the method of Dutch published Patent Application No. 6,902,013 for example by reaction of a 3-methylceph-2-em compound with N-bromosuccinimide to yield the corresponding 3-bromomethylceph-2-em compound.

Where X in formula (IV) is an acetoxy group, such starting materials may be prepared for example by acylation of 7-aminocephalosporanic acid, e.g. in an analogous manner to process (A) above. Compounds of formula (IV) in which X represents other acyloxy groups can be prepared by acylation of the corresponding 3-hydroxymethyl compounds which may be prepared for example by hydrolysis of the appropriate 3-acetoxymethyl compounds e.g. as described inter alia in British patent specifications Nos. 1,474,519 and 1,531,212.

Compounds of formula (II) may likewise be prepared in conventional manner, e.g. by nucleophilic displacement of a corresponding 3-acyloxymethyl or 3-halomethyl compound with an N-carbamoylmethylpyridthione.

A further method for the preparation of starting materials of formula (II) comprises deprotecting the corresponding protected 7β-amino compound in conventional manner, e.g. using POCl$_3$ in methanol or PCl$_5$.

It is to be noted that compounds of formula (II) are novel and constitute a further aspect of the present invention.

The sulphur nucleophile used in process (B) above may be prepared by reacting a bromopyridine, e.g. 4-bromopyridine with iodoacetamide followed by a sulphide or hydrosulphide salt, e.g. sodium sulphide, to give the 1-carbamoylmethylpyridthione, e.g. 1-carbamoylmethylpyrid-4-thione. These sulphur nucleophiles are novel and constitute a still further aspect of the present invention.

It should be appreciated that in some of the above transformations it may be necessary to protect any sensitive groups in the molecule of the compound in question to avoid undesirable side-reactions. For example, during any of the reaction sequences referred to above it may be necessary to protect the NH$_2$ group of the aminothiazolyl moiety, for example by tritylation, acylation (e.g. chloroacetylation), protonation or other conventional method. The protecting group may thereafter be removed in any convenient way which does not cause breakdown of the desired compound, e.g. in the case of a trityl group by using an optionally halogenated carboxylic acid such as acetic acid, formic acid, chloroacetic acid or trifluoroacetic acid or using a mineral acid, e.g. hydrochloric acid or mixtures of such acids, conveniently in the presence of a protic solvent such as water or, in the case of a chloroacetyl group, by treatment with thiourea.

Carboxyl blocking groups used in the preparation of the compounds of formula (I) or in the preparation of necessary starting materials are desirably groups which may readily be split off at a suitable stage in the reaction sequence, conveniently at the last stage. It may, however, be convenient in some instances to employ biologically acceptable, metabolically labile carboxyl blocking groups such as acyloxy-methyl or -ethyl groups (e.g. acetoxy-methyl or -ethyl or pivaloyloxymethyl groups) and retain these in the final product to give a biologically acceptable ester derivative of the compound of formula (I).

Suitable carboxyl blocking groups are well known in the art, a list of representative blocked carboxyl groups being included in British Pat. No. 1,399,086. Preferred blocked carboxyl groups include aryl lower alkoxycarbonyl groups such as p-methoxybenzyloxycarbonyl, p-nitrobenzyloxycarbonyl and diphenylmethoxycarbonyl; t-butoxycarbonyl; and lower haloalkoxycarbonyl groups such as 2,2,2-trichloroethoxycarbonyl. Carboxyl blocking group(s) may subsequently be removed by any of the appropriate methods disclosed in the literature; thus, for example, acid or base catalysed hydrolysis is applicable in many cases, as are enzymically-catalysed hydrolyses.

The following Examples illustrate the invention. All temperatures are in °C. "Ether" refers to diethyl ether, "petrol" refers to petroleum ether (b.p. 40°–60°) "Kieselgel" is chromatographic silica and "Calofort U" is a form of finely divided calcium carbonate. Proton magnetic resonance spectra were determined on the products at 100 MHz. The integrals were in agreement with the assignments; the signs of the coupling constants, J, in Hz, were not determined. The following abbreviations are used:

s=singlet, d=doublet, m=muliplet, br=broad and ABq=AB-quartet.

PREPARATION 1

4-Bromo-1-Carbamoylmethylpyridinium Iodide

A mixture of 4-bromopyridine hydrochloride (980 mg.), water (5 ml.), ether (10 ml.) and potassium hydroxide (400 mg.) was shaken and the separated aqueous layer was extracted with more ether (10 ml.). The combined organic solution was dried ($Na_2SO_4$) and treated with a solution of iodoacetamide (1.4 g.) in acetone (15 ml.). The mixture was left to stand in the dark at 22° for 3 days. The crystals obtained were filtered off, washed with ether and dried in vacuo to give the title compound (308 mg.), $\tau$ (DMSO-$d_6$) 1.04 (d, J 7 Hz) (pyrid-2 and 6-yl), 1.43 (d, J 7 Hz) (pyrid-3 and 5-yl), 1.88 and 2.27 (2 br.s.) ($CONH_2$), 4.52 (s, $N^{\oplus}CH_2$).

PREPARATION 2

1-(Carbamoylmethyl)pyrid-4-thione

4-Bromo-1-carbamoylmethylpyridinium iodide (810 mg.) in ethanol (20 ml.) was treated with anhydrous sodium sulphide (205 mg.) and the mixture was stirred and refluxed for 30 minutes. The mixture was left to cool and was then filtered. The filtrate was treated with ether (60 ml.) and the resulting precipitate was filtered off, washed with ether and dried rapidly in vacuo to give a solid which was purified on a column of silica gel eluted with chloroform: ethanol 1:1. 50 ml. fractions were collected and fractions 4 to 7 were combined and evaporated down to about 10 ml. The mixture was heated briefly to boiling and was then left to cool at 4° overnight. The crystals were filtered off and dried in vacuo to give the title compound (63 mg.), m.p. (Kofler) 260° to 264° (decomp.), $\lambda_{max}$ 235.5 nm ($E_{1\ cm}^{1\%}$ 356), $\lambda_{max}$ 351.5 nm ($E_{1\ cm}^{1\%}$ 1726) $\lambda_{inf}$ 293 nm ($E_{1\ cm}^{1\%}$ 80) (EtOH).

EXAMPLE 1

(a) Diphenylmethyl (1S, 6R, 7R)-7-[(Z)-2-(2-t-Butoxycarbonylprop-2-oxyimino)-2-(2-tritylaminothiazol-4-yl)acetamido]-3-(pyrid-4-ylthiomethyl)ceph-3-em-4-carboxylate, 1-Oxide.

A stirred mixture of diphenylmethyl (1S, 6R, 7R)-3-bromomethyl-7-[(Z)-2-(2-t-butoxycarbonylprop-2-oxyimino)-2-(2-tritylaminothiazol-4-yl)acetamido]ceph-3-em-4-carboxylate,1-oxide (1.54 g) and 4-mercaptopyridine (0.195 g) in dry tetrahydrofuran (12 ml) was treated with triethylamine (0.224 ml) to give a red mixture. After stirring vigorously at 22° for 3 hours, the resultant product was partitioned between ethyl acetate and water (containing a little brine). The organic layer was washed with water (twice) and dried and evaporated in vacuo to give a foam (1.647 g).

This form was purified by chromatography on a column of Merck Kieselgel 60 (70 to 230 mesh, 80 g) which was eluted with toluene:ethyl acetate (3:2) in 80 ml fractions. Appropriate fractions were collected, combined and evaporated to give the title compound (0.92 g) as a foam; $[\alpha]_D$ −7° (c, 0.88, $CHCl_3$), $\lambda_{max}$(EtOH) 255 nm ($E_{1\ cm}^{1\%}$ 252).

(b) Diphenylmethyl (1S, 6R, 7R)-7-[(Z)-2-(2-t-Butoxycarbonylprop-2-oxyimino)-2-(2-tritylaminothiazol-4-yl)acetamido]-3-[(1-carbamoylmethylpyridinium-4-yl)thiomethyl]ceph-3-em-4-carboxylate, 1-oxide, Iodide Salt The product of stage (a) (0.106 g) and iodoacetamide (0.055 g) were suspended to chloroform (0.5 ml) and left to stand at 22° for 18 hours. The mixture was then stirred at 22° for 6 hours and left to stand at ca. 15° for 2½ days. The mixture was diluted with ethyl acetate (ca. 3 ml) and added dropwise to ether (25 ml). The precipitate was filtered off and washed with ether and dried in vacuo to give the title compound (0.105 g) as a solid; $[\alpha]_D$ −14° (c, 0.28, $CHCl_3$) $\nu_{max}$($CHBr_3$) 3550 to 2800 (NH and $NH_2$), 1806 ($\beta$-lactam), 1735 ($CO_2R$), 1690 and 1518 (CONH), 1638 (C=N), 1604 and 1499 (C=C, aromatic) and 755 $cm^{-1}$ (phenyl).

(c) Diphenylmethyl (6R,7R)-7-[(Z)-2-(2-t-Butoxycarbonylprop-2-oxyimino)-2-(2-tritylaminothiazol-4-yl)acetamido]-3-[(1-carbamoylmethylpyridinum-4-yl)thiomethyl]-ceph-3-em-4-carboxylate, Iodide Salt The product of Stage (b) (0.744 g) in acetone (5 ml) was treated with dry powdered potassium iodide (0.4 g).

The stirred and cooled (−10°) mixture was treated with acetyl chloride (0.086 ml) and the product was stirred at 0° to 2° for 1¼ hours. The mixture was added slowly to a stirred solution of sodium metabisulphite (1 g) in water (100 ml) and the precipitate was filtered off and washed with water and dried in vacuo over phosphorus pentoxide to give a solid (0.679 g) containing some starting material.

The reduction sequence was repeated on the product (0.679 g) exactly as described above (except that reaction time at 0° to 2° was 50 minutes) to give a precipitate which was extracted into chloroform. The organic solution was washed with water and dried and evaporated to give the title compound (0.636 g) as a foam, $[\alpha]_D$ −37° C. (c, 0.34, $CHCl_3$), $\lambda_{max}$ (EtOH) 307.5 nm ($E_{1\ cm}^{1\%}$ 170) with an inflection at 260 nm ($E_{1\ cm}^{1\%}$ 163)

and $\nu_{max}$(CHBr$_3$) 3460, 3406 and ca. 3250 (NH and NH$_2$), 1800 ($\beta$-lactam), 1730 to 1690 (broad, CO$_2$R and CONH), 1605 and 1500 (C=C, aromatic) 1528 (CONH) and 760 cm$^{-1}$ (phenyl).

(d) (6R,7R)-7-[(Z)-2-(2-Aminothiazol-4-yl)-2-(2-carboxyprop-2-oxyimino)acetamido]-3-[(1-carbamoylmethylpyridinium-4-yl)thiomethyl]ceph-3-em-4-carboxylate The product of stage (c) (0.53 g) was treated with anisole (1 ml) and trifluoroacetic acid (4 ml) was added thereto. The suspension was swirled for 2 minutes at 22° and was then evaporated to an oil which was triturated with ether and dried in vacuo to give a solid (0.392 g) which was treated with anisole (0.12 ml) followed by trifluoroacetic acid (15 ml). The suspension was swirled occasionally at 22° over 15 minutes and was then filtered. The residue was washed with trifluoroacetic acid (2×5 ml) and the filtrate and washings were evaporated to an oil which on trituration with ether gave a solid which was filtered off, washed with ether and dried in vacuo to give the title compound (0.352 g) as a solid associated with 1.1 moles of trifluoroacetic acid; $[\alpha]_D$−50° (c 0.35, DMSO), $\lambda_{max}$ (pH 6 buffer) 232 nm (E$_1$ $_{cm}$$^{1\%}$ 283) and 308 nm (E$_1$ $_{cm}$$^{1\%}$ 317) with an inflection at 260 nm (E$_1$ $_{cm}$$^{1\%}$ 204).

EXAMPLE 2

(a) Diphenylmethyl (1S,6R,7R)-7-[(Z)-2-(1-t-butoxycarbonylcyclobut-1-oxyimino)-2-(2-tritylaminothiazol-4-yl)acetamido]-3-(pyrid-4-ylthiomethyl)ceph-3-em-4-carboxylate, 1-oxide Diphenylmethyl (1S,6R,7R)-3-bromomethyl-7-[(Z)-2-(1-t-butoxycarbonylcyclobut-1-oxyimino)-2-(2-tritylaminothiazol-4-yl)acetamido]ceph-3-em-4-carboxylate, 1-oxide (4.86 g) in acetone (150 ml) was treated with 4-mercaptopyridine (693 mg) and Calofort U (1.56 g). The mixture obtained was refluxed for 80 minutes, filtered and the residue washed with acetone. The filtrate and washings were evaporated to give a solid which was dissolved in dichloromethane (100 ml) and washed with saturated aqueous sodium hydrogen carbonate (100 ml), water (100 ml), brine (100 ml) and dried over anhydrous sodium sulphate. The solvents were evaporated to give a foam. This was chromatographed on a column of Kieselgel 60 (160 g) and the column eluted with dichloromethane:acetone (3:1). Appropriate fractions were combined and evaporated to give the title compound as a foam (2.98 g), $\nu_{max}$ (CHBr$_3$) 3400 (NH), 1806 ($\beta$-lactam), 1722 (CO$_2$R), 1680 and 1514 cm$^{-1}$ (CONH) and $\tau$ (CDCl$_3$) values include 1.74 and 3.08 (2 doublets; pyridyl protons), 3.00 (s; CHPh$_2$), 3.28 (s; thiazolyl proton), 3.88 (dd, J10 and 5; 7-H), 5.48 (d, J5; 6-H), 5.45 and 6.23 (2 doublets; 3-CH$_2$), 7.46 and 8.0 (multiplets; cyclobutyl protons), 8.55 (s; t-butyl group).

(b) Diphenylmethyl (1S,6R,7R)-7-[(Z)-2-(1-t-butoxycarbonylcyclobut-1-oxyimino)-2-(2-tritylaminothiazol-4-yl)acetamido[-3-[(1-carbamoylmethylpyridinium-4-yl)thiometyl]ceph-3-em-4-carboxylate, 1-oxide, Iodide salt The product of Stage (a) (2.9 g) and iodoacetamide (0.99 g) were dissolved in chloroform (16 ml) and stirred at 21° for 16 hours and then stood at 22° for 3 days. The solution was then added dropwise to stirred ether (500 ml) and filtered to give the title compound as a solid (3.08 g), $\nu_{max}$ (Nujol) 3340 (NH and NH$_2$), 1800 ($\beta$-lactam), 1724 (CO$_2$R), 1690 and 1520 (CONH) and 1690 cm$^{-1}$ (CONH$_2$), $\lambda_{max}$ (EtOH) 309 nm (E$_1$ $_{cm}$$^{1\%}$ 101).

(c) Diphenylmethyl (6R,7R)-7-[(Z)-1-t-butoxycarbonylcyclobut-1-oxyimino)-2-(2-tritylaminothiazol-4-yl)acetamido]-3-[(1-carbamoylmethylpyridinium-4-yl)thiomethyl]ceph-3-em-4-carboxylate, Iodine salt The product of Stage (b) (2.9 g) in acetone (20 ml) was treated with potassium iodide (1.54 g) and the mixture cooled to −10° and treated with acetyl chloride (0.33 ml). The mixture was stirred at 0° to 5° for 2½ hours and then slowly added to a stirred solution of sodium metabisulphite (4 g) in water (10 ml) and the precipitate filtered off, washed with water and dried over phosphorus pentoxide to give the title compound (2.52 g), $\lambda_{max}$ (EtOH) 308 nm (E$_1$ $_{cm}$$^{1\%}$ 157), $\nu_{max}$ (CHBr$_3$) 3460, 3400, 3260 (NH and NH$_2$), 1794 ($\beta$-lactum), 1720 (CO$_2$R), 1700 (CONH$_2$) and 1690 and 1526 cm$^{-1}$ (CONH).

(d) (6R,7R)-7-[(Z)-2-(2-Aminothiazol-4-yl)-2-(1-carboxycyclobut-1-oxyimino)acetamido]-3-[(1-carbamoylmethylpyridinium-4-yl)thiomethyl]ceph-3-em-4-carboxylate The product of Stage (c) (2.05 g) was treated with anisole (4 ml) and trifluoroacetic acid (16 ml). The suspension was swirled at 22° for 2 minutes and the solvents evaporated to give an oil which was triturated with ether to give a solid. This solid was suspended in anisole (2.5 ml) and trifluoroacetic acid (58 ml) and swirled for 15 minutes at 22° and then filtered. The residue was washed with trifluoroacetic acid (2×5 ml) and the filtrate washings evaporated to give an oil which on trituration with ether gave a solid. This was dissolved in trifluoroacetic acid (40 ml) and water (100 ml) was added. The solution was stirred for 30 minutes at 22°, concentrated to ca 60 ml in vacuo and washed with ether (3×100 ml). The aqueous phase was then briefly evaporated and freeze-dried to give the title compound as a solid (1.13 g) associated with 1.5 moles of trifluoroacetic acid, $\lambda_{max}$ (EtOH) 236, 260 and 309.5 nm (E$_1$ $_{cm}$$^{1\%}$ 244, 167 and 257), $\nu_{max}$ (Nujol) 3300 (NH$_2$ and NH), 1780 ($\beta$-lactam), 1670 (CF$_3$CO$_2$−), 2600 and 1720 (CO$_2$H), 1710 (CONH$_2$), 1690 and 1550 cm$^{-1}$ (CONH). The product was further purified by high pressure liquid chromatography and column chromatography.

EXAMPLE 3

(a) Diphenylmethyl (6R,7R)-7-[(Z)-2-(1-t-butoxycarbonylcyclobut-1-oxyimino)-2-(2-tritylaminothiazol-4-yl)acetamido]-3-[(1-carbamoylmethylpyridinium-4-yl)thiomethyl]ceph-3-em-4-carboxylate, Bromide Diphenylmethyl (6R,7R)-3-bromomethyl-7-[(Z)-2-(1-t-butoxycarbonylcyclobut-1-oxyimino)-2-(2-tritylaminothiazol-4-yl)acetamido]ceph-3-em-4-carboxylate (300 mg.) in dry tetrahydrofuran (5 ml.) was treated with 1-carbamoylmethylpyrid-4-thione (53 mg.) and the suspension obtained was stirred at 22° for 24 hours. The reaction mixture was diluted with chloroform (10 ml.), filtered and the filtrate was evaporated down to about 2 ml., then diluted with petrol (10 ml.)

The fine precipitate was filtered off and dried in vacuo to give the title compound (284 mg.) as a solid, $[\alpha]_D$ $-54°$ (c 0.47, CHCl$_3$), $\lambda_{max}$ 310 nm (E$_{1\,cm}^{1\%}$ 197), $\lambda_{inf}$ 236 nm (E$_{1\,cm}^{1\%}$ 250), $\lambda_{inf}$ 258 nm (E$_{1\,cm}^{1\%}$ 175) (EtOH)

(b)
(6R,7R)-7-[(Z)-2-(2-Aminothiazol-4-yl)-2-(1-carboxycyclobut-1-oxyimino)acetamido]-3-[(1-carbamoylmethylpyridinium-4-yl)thiomethyl]ceph-3-em-4-carboxylate The above product from stage (a) (1.17 g) was treated with anisole (1.2 ml.) and trifluoroacetic acid (4.8 ml.) and the mixture obtained was swirled at 22° for 5 minutes until the solid had dissolved. The solution was evaporated to an oil which was triturated with ether to give a solid. The solid was moistened with anisole (0.12 ml.) and treated with trifluoroacetic acid (12 ml.). The resultant solution was left to stand at 22° for 15 minutes and was then evaporated to an oil which was triturated with ether (50 ml.). The solid was filtered off, washed with ether and dried in vacuo. The residue was treated with warm (30°) trifluoroacetic acid:water=1:4 (50 ml.) and the faint suspension was swirled at 30° for 10 minutes and was then washed with ethyl acetate (50 ml.). The clear aqueous layer was washed with ether (50 ml.) and then concentrated by evaporation and freeze dried to give the title compound associated with trifluoroacetic acid (375 mg.) as a foam $[\alpha]_D$ $-14°$ (c 0.52, H$_2$O:EtOH=1:1), $\lambda_{max}$ 235 nm (E$_{1\,cm}^{1\%}$ 250), $\lambda_{max}$ 309.5 nm (E$_{1\,cm}^{1\%}$ 329), $\lambda_{inf}$ 255 nm (E$_{1\,cm}^{1\%}$ 188) (pH 6.4 buffer).

EXAMPLE 4

(6R,7R)-7-[(Z)-2-(2-Aminothiazol-4-yl)-2-(1-carboxycyclobut-1-oxyimino)acetamido]-3-[(1-carbamoylmethylpyridinium-4-yl)thiomethyl]ceph-3-em-4-carboxylate sodium salt A mixture of (6R,7R)-3-acetoxymethyl-7-[(Z)-2-(aminothiazol-4-yl)-2-(1-carboxycyclobut-1-oxyimino)acetamido]ceph-3-em-4-carboxylic acid hydrate (1.165 g), 1-(carbamoylmethyl)pyrid-4-thione (697 mg) and sodium bicarbonate (659 mg) in water (2 ml) was stirred at 80° C. under nitrogen for 1.¼ h. The solution obtained was cooled, diluted with water and then added dropwise with stirring to acetone (600 ml) to give a solid.

A solution of this solid in water (30 ml) was chromatographed on a column of Amberlite XAD-2 resin. The column was eluted with water (1400 ml) followed by water:ethanol (3:1; 800 ml), 200 ml fractions being taken. Fractions 6–11 were combined, concentrated by evaporation and freeze dried to give the title compound as a foam (525 mg), $[\alpha]_D$ $-9°$ (c 0.94, water), $\lambda_{max}$ (pH 6.4 buffer) 235.5 nm (E$_{1\,cm}^{1\%}$ 304) and 309 nm (E$_{1\,cm}^{1\%}$ 295), inflection at 250 nm (E$_{1\,cm}^{1\%}$ 255).

EXAMPLE 5

(6R,7R)-7-[(Z)-2-(2-Aminothiazol-4-yl)-2-(2-carboxyprop-2-oxyimino)acetamido]-3-[(1-carbamoylmethylpyridinium-4-yl)thiomethyl]ceph-3-em-4-carboxylate, sodium salt (6R,7R)-3-Acetoxymethyl-7-[(Z)-2-(2-aminothiazol-4-yl)-2-(2-carboxyprop-2-oxyimino)acetamido]ceph-3-em-4-carboxylic acid hydrochloride (564 mg), sodium bicarbonate (275 mg), water (1 ml), 1-(carbamoylmethyl)pyrid-4-thione (335 mg) and sodium iodide (1.8 g) were heated together at 80° for 1.¼ hours. The solution was allowed to cool to room temperature, water (1 ml) was added and the solution added dropwise to stirred acetone (250 ml). The precipitate obtained was filtered off, washed with acetone and ether and dried in vacuo.

The above solid was purified on a column of Amberlite XAD-2 (60 g) eluting first with water (7×60 ml fractions) and then water-ethanol 3:1 (5×60 ml fractions). The latter fractions were combined and concentrated by evaporation and finally freeze dried to give the title compound as a foam (253 mg) $[\alpha]_D$ $-14°$ (c 0.5, H$_2$O), $\lambda_{max}$ 234.5 nm (E$_{1\,cm}^{1\%}$ 338), $\lambda_{max}$ 309 nm (E$_{1\,cm}^{1\%}$ 338), $\lambda_{inf}$ 254 nm (E$_{1\,cm}^{1\%}$ 249) (pH 6 buffer).

EXAMPLE 6

(a) Diphenylmethyl (1S,6R,7R)-7-formamido-3-(pyrid-4-yl)thiomethylceph-3-em-4-carboxylate 1-oxide, Iodide Diphenylmethyl (1S,6R,7R)-3-bromomethyl-7-formamidoceph-3-em-4-carboxylate (3.03 g) in acetone (100 ml) was treated with 4-mercaptopyridine (1.0 g) and "Calofort U" (1.2 g). The mixture was stirred and refluxed under nitrogen for 20 minutes, and it was then filtered. The filtrate was evaporated to a foam. The residue from the filtration was shaken with chloroform (250 ml) and water (150 ml), was filtered again and the filtrate was added to the foam. The aqueous phase of the mixture was treated with sodium bicarbonate solution until it was at pH 7. A little sodium chloride solution was added to clear the emulsion, then the organic phase was separated, washed, (water, 100 ml) dried (Na$_2$SO$_4$) and evaporated to a crystalline solid. The solid was triturated with ether (ca 100 ml) and then filtered off and dried in vacuo to give the title compound (2.68 g), $[\alpha]_D$ $+39°$ (c 0.93, CHCl$_3$), m.p. (Kofler) 152° to 156° (with decomp.).

(b) Diphenylmethyl (1S,6R,7R)-3-[(1-carbamoylmethylpyridinium-4-yl)thiomethyl]-7-formamidoceph-3-em-4-carboxylate, 1-oxide, iodide The product from stage (a) (2.4 g) in N,N-dimethylformamide (12 ml) was treated with iodoacetamide (1.6 g) and the solution obtained was left to stand in the dark at 22° for 30 hours. The solution was added slowly to stirred ethyl acetate (250 ml) and the precipitate thus formed was filtered off and washed with ethyl acetate (2×75 ml) and ether (50 ml). The solid was then dried in vacuo to give the title compound (3.13 g) as a solid, $[\alpha]_D$ $-54°$ (c 0.47, CHCl$_3$, $\lambda_{max}$ 311 nm (E$_{1\,cm}^{1\%}$ 118), $\lambda_{max}$ 266 nm (E$_{1\,cm}^{1\%}$ 104), $\lambda_{max}$ 457 nm (E$_{1\,cm}^{1\%}$ 391), $\lambda_{inf}$ 251 nm (E$_{1\,cm}^{1\%}$ 107), $\lambda_{inf}$ 257 nm (E$_{1\,cm}^{1\%}$ 105) (EtOH).

(c) Diphenylmethyl (1S,6R,7R)-7-amino-3-[(1-carbamoylmethylpyridinium-4-yl)thiomethyl]cepth-3-em-4-carboxylate, 1-oxide, Iodide, Hydrochloride The product from stage (b) (5.74 g), in methanol (80 ml) was stirred at 0° and to the suspension obtained was added phosphoryl chloride (2.5 ml) dropwise over 10 minutes. The mixture was stirred vigorously at 0° for 2 hours and was then diluted with ether (200 ml). The solid obtained was filtered off and washed with ether (3×50 ml) then dried in vacuo. This solid was resuspended in methanol (80 ml) and treated with phosphoryl chloride (2.5 ml) as above, with the same work-up to give a solid (4.75 g). The solid was triturated with ether (100 ml), filtered off, washed with ether (2×50 ml) and dried in vacuo to give the title compound (4.50 g), $[\alpha]_D +18°$ (c 0.32, H$_2$O), $\lambda_{max}$ 310.5 nm (E$_1$ $_{cm}$$^{1\%}$ 359), $\lambda_{inf}$ 274 nm (E$_1$ $_{cm}$$^{1\%}$ 124), $\lambda_{inf}$ 234 nm (E$_1$ $_{cm}$$^{1\%}$ 178), $\lambda_{inf}$ 262 nm (E$_1$ $_{cm}$$^{1\%}$ 107) (EtOH).

(d) Diphenylmethyl (1S,6R,7R)-7-[(Z)-2-(1-t-butoxycarbonylcyclobut-1-oxyimino)-2-(2-tritylaminothiazol-4-yl)acetamido]-3-[(1-carbamoylmethylpyridinium-4-yl)thiomethyl]ceph-3-em-4-carboxylate, 1-oxide, iodide A solution of (Z)-2-(1-t-butoxycarbonylcyclobut-1-oxyimino)-2-(2-tritylaminothiazol-4-yl)acetic acid (583 mg) in dry tetrahydrofuran (7 ml) was treated with 1-hydroxybenztriazole monohydrate (148 mg) and N,N'-dicyclohexylcarbodiimide (247 mg) and the mixture was stirred at 22° for 30 minutes.

The product from stage (c) (730 mg) was dissolved in N,N-dimethylformamide (20 ml) and propylene oxide (0.1 ml) was added thereto. The tetrahydrofuran mixture was filtered into the dimethylformamide solution. The resulting solution was treated with more propylene oxide (0.1 ml) and was then stirred at 22° for 2 hours and finally left to stand at 22° for a further 16 hours. The solution was concentrated slightly by evaporation and was partitioned between chloroform (150 ml) and 1 N hydrochloric acid (150 ml). The organic layer was washed with 2 N hydrochloric acid, water and brine and was then dried (Na$_2$SO$_4$) and evaporated to an oil, which was added slowly to stirred ether (150 ml). The resulting precipitate was filtered off, washed with ether and dried in vacuo to give the title compound (650 mg) as a solid $[\alpha]_D$ −111° (c 0.34, CHCl$_3$). The sample was identical with the product of Example 2(b) by HPLC.

(e) Diphenylmethyl (6R,7R)-7-[(Z)-2-(1-t-butoxycarbonylcyclobut-1-oxyimino)-2-(2-tritylaminothiazol-4-yl)acetamido]-3-[(1-carbamoylmethylpyridinium-4-yl)thiomethyl]ceph-3-em-4-carboxylate, iodide A solution of the product of stage (d) (503 mg) in dry N,N-dimethylformamide (3 ml) was treated with dry potassium iodide (330 mg) and the solution was cooled to −10° then treated with acetyl chloride (0.075 ml). The mixture was stirred at 0° to 5° for 1 hour and was then added slowly to a stirred solution of sodium metabisulphite (0.5 g) in water (50 ml). The precipitate obtained was filtered off, washed with water and then partitioned between chloroform (100 ml) and dilute sodium metabisulphite solution (100 ml). The organic layer was washed with water and brine then dried (Na$_2$SO$_4$) and evaporated to a glass which was dissolved in chloroform (3 ml). The solution was added slowly to stirred petrol (75 ml) and the precipitate obtained was filtered off and washed with petrol, then dried in vacuo to give a solid.

The solid was dissolved in acetone (2 ml) and treated with dry powdered potassium iodide (220 mg) and acetyl chloride (0.05 ml), stirred for one hour, then diluted with a solution of sodium metabisulphite (0.5 g) in water (50 ml) and worked up as described above to give the title compound (285 mg) as a solid, $[\alpha]_D$ −95° (c 0.29, CHCl$_3$), $\lambda_{max}$ 312 nm (E$_1$ $_{cm}$$^{1\%}$ 180), $\lambda_{inf}$ 260 nm (E$_1$ $_{cm}$$^{1\%}$ 189) (CHCl$_3$).

(f) (6R,7R)-7-[(Z)-2-(2-Aminothiazol-4-yl)-2-(1-carboxycyclobut-1-oxyimino)acetamido]-3-[(1-carbamoylmethylpyridinium-4-yl)thiomethyl]ceph-3-em-4-carboxylate The product from stage (e) (220 mg) was treated with anisole (0.25 ml) and then with trifluoroacetic acid (1 ml) and worked-up substantially as described in Example 3(b) to give the title compound associated with trifluoroacetic acid (52 mg) as a foam, $\lambda_{max}$ 233 nm (E$_1$ $_{cm}$$^{1\%}$ 239), $\lambda_{max}$ 308.5 nm (E$_1$ $_{cm}$$^{1\%}$ 259), $\lambda_{inf}$ 254 nm (E$_1$ $_{cm}$$^{1\%}$ 192) (pH 6 buffer). The NMR spectrum resembled that of the product of Example 3(b).

PHARMACEUTICAL FORMULATIONS

The antibiotic compounds of the invention may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers if necessary with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle, e.g. sterile, pyrogen-free water, before use.

If desired, such powder formulations may contain an appropriate non-toxic base in order to improve the water-solubility of the active ingredient and/or to ensure that when the powder is constituted with water, the pH of the resulting aqueous formulation is physiologically acceptable. Alternatively the base may be present in the water with which the powder is constituted. The base may be for example an inorganic base such as sodium carbonate, sodium bicarbonate or sodium acetate or an organic base such as lysine or lysine acetate.

The antibiotic compounds may also be formulated as suppositories e.g. containing conventional suppository bases such as cocoa butter or other glycerides.

For medication of the eyes or ears, the preparations may be formulated as individual capsules, in liquid or semi-solid form, or as drops.

Compositions for veterinary medicine may also, for example, be formulated as intramammary preparations in either long acting or quick-release bases.

The compositions may contain from 0.1% upwards, e.g. 0.1–99% of the active material, depending on the method of administration. When the compositions comprise dosage units, each unit will preferably contain 50–1500 mg of the active ingredient. The dosage as employed for adult human treatment preferably ranges from 250 to 6000 mg per day, depending on the route and frequency of administration. For example, in adult human treatment 1000 to 3000 mg per day administered intravenously or intramuscularly should normally suffice. In treating Pseudomonas infections higher daily doses may be required.

The antibiotic compounds according to the invention may be administered in combination with other therapeutic agents such as antibiotics, for example penicillins or ether cephalosporins.

The following formulations illustrate how the compounds according to the invention may be made up into pharmaceutical formulations.

EXAMPLE A

Formulation for Injection

Fill sterile (6R,7R)-7-[(Z)-2-(2-aminothiazol-4-yl)-2-(carboxyprop-2-oxyimino)acetamido]-3-[(1-carbamoylmethylpyridinium-4-yl)thiomethyl]ceph-3-em-4-carboxylate monosodium salt into glass vials such that each vial contains an amount equivalent to 500 mg of the antibiotic acid. Carry out the filling aseptically under a blanket of sterile nitrogen. Close the vials using rubber discs, or plugs, held in position by aluminium overseals thereby preventing gaseous exchange or ingress of microorganisms. Constitute the product by dissolving in Water for Injections or other suitable sterile vehicle shortly before administration.

EXAMPLE B

Formulation for Injection

A similar formulation may be prepared as in Example A using (6R,7R)-7-[(Z)-2-(2-aminothiazol-4-yl)-2-(1-carboxycyclobut-1-oxyimino)acetamido]-3-[(1-carbamoylmethylpyridinium-4-yl)thiomethyl]ceph-3-em-4-carboxylate, monosodium salt; such that each vial contains an amount equivalent to 1.0 g of the antibiotic acid.

EXAMPLE C

Formulation for Injection

Formula per vial (6R,7R)-7-[(Z)-2-(2-Aminothiazol-4-yl)-2-(2-carboxyprop-2-oxyimino)acetamido]-3-[(1-carbamoylmethylpyridinium-4-yl)thiomethyl]ceph-3-em-4-carboxylate . . . 1.00 g.
Sodium carbonate, anhydrous . . . 100 mg

METHOD

Blend the sterile cephalosporin antibiotic with sterile sodium carbonate under aseptic conditions. Fill aseptically into glass vials under a blanket of sterile nitrogen. Close the vials using rubber discs or plugs, held in position by aluminium overseals, thereby preventing gaseous exchange or ingress of microorganisms. Constitute the product by dissolving in Water for Injections or other suitable sterile vehicle shortly before administration.

EXAMPLE D

Formulation for Injection

Formula per vial (6R,7R)-7-[(Z)-2-(2-Aminothiazol-4-yl)-2-(1-carboxycyclobut-1-oxyimino)acetamido]-3-[(1-carbamoylmethylpyridinium-4-yl)thiomethyl]ceph-3-em-4-carboxylate 500 mg.
Lysine Acetate . . . 191 mg.

METHOD

As in Example C.

We claim:

1. A cephalosporin antibiotic selected from the group consisting of compounds of the formula

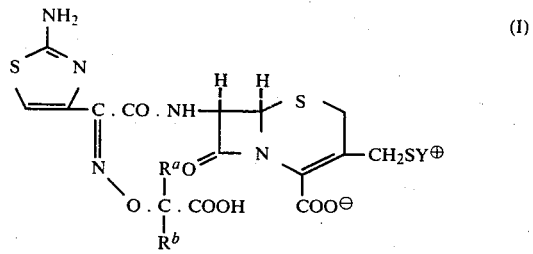

(wherein $R^a$ and $R^b$, which may be the same or different, each represents a $C_{1-2}$ alkyl group, or together with the carbon atom to which they are attached form a $C_{3-6}$ cycloalkylidene group and $Y^\oplus$ represents an N-carbamoylmethylpyridinium group) and non-toxic salts and non-toxic metabolically labile esters thereof.

2. Compounds as claimed in claim 1 wherein $Y^\oplus$ represents a 1-carbamoylmethylpyridinium-4-yl group.

3. Compounds as claimed in claim 1 wherein $R^a$ and $R^b$ both represent methyl groups.

4. Compounds as claimed in claim 1 wherein $R^a$ and $R^b$, together with the carbon atom to which they are attached, form a cyclobutylidene group.

5. A cephalosporin antibiotic of claim 1 which is (6R,7R)-7-[(Z)-2-(2-aminothiazol-4-yl)-2-(2-carboxyprop-2-oxyimino)acetamido]-3-[(1-carbamoylmethylpyridinium-4-yl)thiomethyl]ceph-3-em-4-carboxylate.

6. The non-toxic salts of the cephalosporin antibiotic claimed in claim 5.

7. A cephalosporin antibiotic of claim 1 which is (6R,7R)-7-[(Z)-2-(2-aminothiazol-4-yl)-2-(1-carboxycyclobut-1-oxyimino)acetamido]-3-[(1-carbamoylmethylpyridinium-4-yl)thiomethyl]ceph-3-em-4-carboxylate.

8. The non-toxic salts of the cephalosporin antibiotic claimed in claim 7.

9. A method of combating a bacterial infection in a warm blooded animal comprising administering to said animal an antibacterially effective amount of at least one cephalosporin antibiotic as claimed in claim 1.

* * * * *